(12) United States Patent
Cardot et al.

(10) Patent No.: US 11,155,548 B2
(45) Date of Patent: Oct. 26, 2021

(54) HYDROCODONE BASE AND METHODS FOR ITS PURIFICATION

(71) Applicant: Noramco, LLC, Wilmington, DE (US)

(72) Inventors: Jessica Cardot, Hull, GA (US); Joshua Sasine, Bishop, GA (US); Paul Nichols, Watkinsville, GA (US)

(73) Assignee: NORAMCO, LLC, Wilmington, DE (US)

( * ) Notice: Subject to any disclaimer, the term of this patent is extended or adjusted under 35 U.S.C. 154(b) by 0 days.

(21) Appl. No.: 16/498,196

(22) PCT Filed: Mar. 27, 2018

(86) PCT No.: PCT/IB2018/052103
§ 371 (c)(1),
(2) Date: Sep. 26, 2019

(87) PCT Pub. No.: WO2018/178879
PCT Pub. Date: Oct. 4, 2018

(65) Prior Publication Data
US 2020/0031826 A1    Jan. 30, 2020

Related U.S. Application Data

(60) Provisional application No. 62/477,035, filed on Mar. 27, 2017.

(51) Int. Cl.
*C07D 489/02* (2006.01)
*C07D 471/08* (2006.01)
*C07D 489/04* (2006.01)

(52) U.S. Cl.
CPC ......... *C07D 471/08* (2013.01); *C07D 489/02* (2013.01); *C07D 489/04* (2013.01)

(58) Field of Classification Search
CPC .................................................... C07D 489/02
USPC ........................................................ 546/45
See application file for complete search history.

(56) References Cited

U.S. PATENT DOCUMENTS

2004/0157784 A1    8/2004   Chopdekar et al.
2011/0071297 A1    3/2011   Orr et al.

FOREIGN PATENT DOCUMENTS

| AU | 2003200858 B2 | 6/2003 |
| AU | 2015200090 A1 | 2/2015 |
| WO | WO 2017/009865 A1 | 1/2017 |

OTHER PUBLICATIONS

Hailes et al., "Biological Synthesis of the Analgesic Hydromorphone, an Intermediate in the Metabolism of Morphine, by Pseudomonas putida M10," Applied and Environmental Microbiology, 59(7):2166-2170, (1993).

WIPO Application No. PCT/IB18/52103, PCT International Search Report and Written Opinion of the International Searching Authority dated Jul. 27, 2018.

*Primary Examiner* — Charanjit Aulakh

(74) *Attorney, Agent, or Firm* — Alston & Bird LLP

(57) ABSTRACT

A method of recovering a highly pure hydrocodone base from an impure hydrocodone preparation includes contacting the impure hydrocodone preparation with a weak acid in water to form a solution and adding a strong base to the solution in an amount sufficient to precipitate the pure hydrocodone base product. A highly pure hydrocodone base comprises less than 0.0025 wt % codeinone.

9 Claims, No Drawings

HYDROCODONE BASE AND METHODS FOR ITS PURIFICATION

CROSS REFERENCE TO RELATED APPLICATIONS

This patent application is a national stage application filed under 35 U.S.C. § 371 of International Application No. PCT/IB2018/052103, filed Mar. 27, 2018, which claims the benefit of priority to U.S. Provisional Patent Application No. 62/477,035, filed Mar. 27, 2017, each of which is hereby incorporated by reference in its entirety for all purposes.

BACKGROUND OF THE INVENTION

The present invention generally relates to methods of purifying opioids and, more particularly, to a method for purifying hydrocodone base.

Current methods of preparing and purifying hydrocodone base result in levels of impurities, and of codeinone in particular, that exceed desired levels for commercial application. Thus, there is a need for a more efficient method to isolate highly pure hydrocodone base.

BRIEF SUMMARY OF THE INVENTION

According to an embodiment of the invention, a method of recovering a highly pure hydrocodone base from an impure hydrocodone preparation includes contacting the impure hydrocodone preparation with a weak acid in water to form a solution; and adding a strong base to the solution in an amount sufficient to precipitate the pure hydrocodone base. The amount of strong base may be sufficient to attain a pH of the solution of about 7 to about 12.5. The method may further include heating the solution before precipitating the highly pure hydrocodone (i.e., before adding the strong base). In some embodiments the solution is heated to about 40° C. to about 80° C. The method may further include cooling the solution after adding the strong base. In some embodiments the solution is cooled to about 20° C. to about 40° C.

In some embodiments, the weak acid is acetic acid, acetoacetic acid, acrylic acid, adipic acid, ascorbic acid, benzoic acid, carbonic acid, citric acid, formic acid, glutaric acid, glycolic acid, glyoxylic acid, glyceric acid, hydrofluoric acid, hydrogen sulfate ion, 3-hydroxypropanoic acid, itaconic acid, lactic acid, malic acid, malonic acid, methymalonic acid, mesaconic acid, methanoic acid, nitrous acid, oxalic acid, phosphoric acid, propionic acid, succinic acid, sulfurous acid, tartaric acid, or a mixture of any of the foregoing. In some embodiments the weak acid is acetic acid, tartaric acid, or a mixture thereof.

In some embodiments, the strong base is lithium hydroxide, sodium hydroxide, potassium hydroxide, magnesium hydroxide, calcium hydroxide, strontium hydroxide, ammonium hydroxide, barium hydroxide, or a mixture of any of the foregoing. In some embodiments the strong base is sodium hydroxide, ammonium hydroxide, or a mixture of any of the foregoing.

In some embodiments the method further includes charging the solution with an organic solvent before the addition of the strong base. The organic solvent may be an alcohol, for example, the organic solvent may be methanol, ethanol, propanol, isopropanol, butanol, tert-butyl alcohol, or a mixture of any of the foregoing. In some embodiments the organic solvent is ethanol, butanol, or a mixture thereof.

The recovered highly pure hydrocodone base may include about 0.05 wt % or less 6α-tetrahydrothebaine (6α-THT). The highly pure hydrocodone base may include about 0.05 wt % or less 6,7-dihydrothebaine (6,7-DHT). The recovered highly pure hydrocodone base may include about 0.05 wt % or less 6β-tetrahydrothebaine base (6β-THT). The recovered highly pure hydrocodone base may include about 0.05 wt % or less p-toluene sulfonylhydrazone of hydrocodone (pT-SHH). The recovered highly pure hydrocodone base may include about 0.0025 wt % or less codeinone. The recovered highly pure hydrocodone base may have a purity of about 99.9% area as measured by high performance liquid chromatography.

According to an embodiment of the invention, a highly pure hydrocodone base is prepared in accordance with a method described herein. According to an embodiment of the invention, a composition includes hydrocodone base, wherein the hydrocodone base has a purity of about 99.9% or greater. In some embodiments the hydrocodone base includes less than 0.0025 wt % codeinone.

DETAILED DESCRIPTION OF THE INVENTION

According to an embodiment of the method described herein, highly pure hydrocodone base is recovered from a hydrocodone base preparation by contacting the impure hydrocodone preparation with a weak acid in water to form a solution and adding a strong base to the solution. According to an embodiment of the method described herein, highly pure hydrocodone base is recovered from a hydrocodone base preparation by contacting the impure hydrocodone base preparation with a weak acid in water to form a solution, heating the solution, and adding a strong base to the solution. In some such embodiments a co-solvent is charged with the solution while the solution is heated and/or immediately before addition of the strong base.

According to an embodiment of the method described herein, highly pure hydrocodone base is recovered from a hydrocodone base preparation by contacting the impure hydrocodone preparation with a weak acid in water to form a solution. It has unexpectedly been found that use of a weak acid reduces codeinone content by about 20-60 wt %. As used herein, "hydrocodone base preparation" refers to a hydrocodone base composition prepared by a conventional process and comprising one or more impurities. A hydrocodone base preparation may comprise at least 0.03, 0.05, 0.1, 0.2, 0.5, 0.75, 1, 2, 5, 10, or 12 wt % of an impurity. Impurities may be any substance other than hydrocodone base, for example, impurities existing in the starting material, impurities formed in a side reaction, intermediates, or excess reagents or solvents from the preparation process and include, but are not limited to: 10-hydroxyhydrocodone base, 10-ketohydrocodone base, 6β-tetrahydrothebaine base, 7-diphenylmethylene-7,8-dihydrothebaine base, codeine-6-methyl ether base (EP impurity F), codeine base (EP Impurity C), codeinone base (EP Impurity E), dihydrocodeine base (EP impurity B), dihydrothebaine base, hydrocodone-N-oxide, hydromorphone base, methylene bridged hydromorphone dimer base, methylene bridged morphine dimer base, morphine base (EP Impurity A), oxycodone base (EP Impurity D), pseudohydrocodone base, thebaine alkaloid (EP Impurity I), 6α-tetrahydrothebaine; 6,7-dihydrothebaine, 8-14-dihydrothebaine, p-toluene sulfonylhydrazone of hydrocodone, norhydrocodone and mixtures of any of the foregoing.

The term "weak acid" has its ordinary meaning and can include, for example, acetic acid, acetoacetic acid, acrylic acid, adipic acid, ascorbic acid, benzoic acid, carbonic acid, citric acid, formic acid, glutaric acid, glycolic acid, glyoxylic acid, glyceric acid, hydrofluoric acid, hydrogen sulfate ion, 3-hydroxypropanoic acid, itaconic acid, lactic acid, malic acid, malonic acid, methymalonic acid, mesaconic acid, methanoic acid, nitrous acid, oxalic acid, phosphoric acid, propionic acid, succinic acid, sulfurous acid, and tartaric acid. The term "weak acid" as used herein also includes salts formed from hydrocodone and a weak acid, for example, hydrocodone acetate, hydrocodone tartrate, and hydrocodone bitartrate. In some embodiments a weak acid comprises tartaric acid, acetic acid, or a mixture thereof. As used herein, "weak acid" may also include mixtures of two or more weak acids, for example any of the foregoing.

The weak acid can be added in an amount of about 0.1 eq, about 0.2 eq, about 0.3 eq, about 0.4 eq, about 0.5 eq, about 0.6 eq, about 0.7 eq, about 0.8 eq, about 0.9 eq, about 1.0 eq, about 1.1 eq, about 1.2 eq, about 1.3 eq, about 1.4 eq, about 1.5 eq, about 1.6 eq, about 1.7 eq, about 1.8 eq, about 1.9 eq, about 2.0 eq, about 2.5 eq, or about 3.0 eq to hydrocodone base. The weak acid can be added in an amount of about 0.01 eq to about 5.0 eq, about 0.1 eq to about 1.0 eq, about 1.0 eq to about 2.0 eq, about 2.0 eq to about 3.0 eq, about 0.1 eq to about 3.0 eq, about 0.1 eq to about 2.0 eq, about 0.5 eq to about 1.5 eq, about 0.75 eq to about 1.25 eq, or about 1.0 eq to about 1.2 eq to hydrocodone base. In some embodiments the weak acid is added in an amount sufficient to attain a pH of about 1.4, about 1.6, about 1.8, about 2.0, about 2.2, about 2.4, about 2.6, about 2.8, about 3.0, about 3.2, about 3.4, about 3.6, about 3.8, about 4, about 4.2, about 4.4, about 4.6, about 4.8, about 5.0, about 5.2, about 5.4, about 5.6, about 5.8, about 6.0, about 6.2, about 6.4, about 6.4, about 6.6, about 6.8, or about 7.0. In some embodiments the weak acid is added in an amount sufficient to attain a pH in a range of from about 1.4 to about 7.0, about 2.0 to about 7.0, about 2.5 to about 7.0, about 3.0 to about 7.0, about 3.5 to about 7.0, about 4.0 to about 7.0, about 4.0 to about 6.0, about 5.0 to about 6.0, about 6.0 to about 7.0, about 4.0 to about 4.5, about 4.5 to about 5.0, about 5.0 to about 5.5, or about 5.5 to about 6.0.

The impure hydrocodone preparation and weak acid may be contacted in water. In some embodiments water is provided in a ratio of impure hydrocodone base (g) to water (mL) of about 1:20, about 1:15, about 1:10, about 1:9, about 1:8, about 1:7, about 1:6, about 1:5, about 1:4, about 1:3, about 1:2, or about 1:1. In some embodiments water is provided in a ratio of impure hydrocodone base (g) to water (mL) of about 1:4 to about 1:6, about 1:3 to about 1:7, about 1:2 to about 1:8, or about 1:1 to about 1:10.

At various steps in the method the solution may be heated. For example, the solution may be heated while the impure hydrocodone preparation is contacted with the weak acid in water. The solution may be heated before and/or during the addition of the strong base. In some embodiments the term "heated" refers to being raised to any temperature greater than room temperature, for example any temperature greater than about 20° C. In some embodiments the solution is heated to a temperature greater than about 25° C., about 30° C., about 35° C., about 40° C., about 45° C., about 50° C., about 55° C., or about 60° C. In some embodiments the solution is heated to a temperature of about 25° C. to about 70° C., about 30° C. to about 60° C., about 40° C. to about 60° C., about 40° C. to about 50° C., or about 45° C. to about 50° C.

In some embodiments the solution may be charged with a co-solvent, either before heating, during heating, or after heating. In some embodiments the co-solvent is an organic solvent, for example, an alcohol such as methanol, ethanol, propanol, isopropanol, butanol, or tert-butyl alcohol. A co-solvent may also include a mixture of two or more solvents, for example any of the foregoing.

In some embodiments a base is added to the solution. In some embodiments the base comprises or consists essentially of a strong base, for example, lithium hydroxide, sodium hydroxide, potassium hydroxide, magnesium hydroxide, calcium hydroxide, strontium hydroxide, ammonium hydroxide, and barium hydroxide. In an embodiment the base comprises or consists essentially of sodium hydroxide or ammonium hydroxide. In other embodiments the base may comprise or consist essentially of a mixture of two or more strong bases, for example any of the foregoing. The base may be added in any suitable concentration (w/w or w/v), for example, about 5%, about 10%, about 12%, about 14%, about 15%, about 16%, about 17%, about 18%, about 19%, about 20%, about 21%, about 23%, about 25%, about 30%, about 35%, about 40%, about 45%, about 50%, about 55%, about 60%, about 65%, about 70%, about 75%, about 80%, about 85%, about 90%, about 95%, or about 100%. In some embodiments the base may be added in a concentration of about 5% to about 75%, about 10% to about 60%, about 10% to about 25%, about 40% to about 60%, about 15% to about 20%, about 45% to about 55%, about 17% to about 19%, or about 48% to about 52%.

A base may be added to the solution in an amount sufficient to attain a basic pH. In some embodiments a base may be added to the solution in an amount sufficient to attain a pH of about 7 to about 12.5, about 7 to about 12, about 7.5 to about 12, about 8 to about 12, about 8 to about 11, about 8 to about 10, about 9 to about 11, about 9 to about 10, about 9.3 to about 9.7, about 9.0, about 9.1, about 9.2, about 9.3, about 9.4, about 9.5, about 9.6, about 9.7, about 9.8, about 9.9, or about 10. The base may be added substantially instantly or over a period of time, for example about 1 minute, about 2 minutes, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about an hour, about 1.5 hours, about 2 hours, about 2.5 hours, about 3 hours, about 3.5 hours, about 4 hours, about 4.5 hours, or about 5 hours. In some embodiments the base is added over a period of time from about 1 minute to about an hour, about 15 minutes to about 45 minutes, about 25 minutes to about 35 minutes, about 1 minute to about 10 minutes, about 10 minutes to about 20 minutes, about 20 minutes to about 30 minutes, about 30 minutes to about 40 minutes, about 40 minutes to about 50 minutes, about 50 minutes to about 60 minutes, about 0.5 hour to about 5 hours, about 1 hour to about 4 hours, or about 2 hours to about 3 hours.

After the base has been added to the solution, the solution may be cooled. In some embodiments, "cooled" refers to any temperature less than the temperature of the solution during or immediately after addition of the base. In some embodiments the term "cooled" refers to being lowered to room temperature, for example about 20° C. In some embodiments the solution is cooled to a temperature less than about 60° C., less than about 55° C., less than about 50° C., less than about 45° C., less than about 40° C., less than about 35° C., less than about 30° C., or less than about 25° C. In some embodiments the solution is cooled to a temperature of about 10° C. to about 45° C., about 20° C. to about 40° C., about 25° C. to about 40° C., about 30° C. to about 40° C., or about 35° C. to about 40° C.

In some embodiments, addition of a strong base to the solution will cause the highly pure hydrocodone base to precipitate from the solution. The highly pure hydrocodone base can be separated from the supernatant by filtration with a membrane, such as a microporous membrane, an ultrafilter membrane, or a reverse osmosis membrane. In some embodiments the highly pure hydrocodone base is filtered from the supernatant and dried in an oven. The highly pure hydrocodone base may be dried in an oven at a temperature of about 25° C., about 30° C., about 35° C., about 40° C., about 45° C., about 50° C., about 55° C., about 60° C., about 65° C., about 70° C., about 75° C., or about 80° C., or greater than about 80° C. In some embodiments the oven is heated to a temperature of about 25° C. to about 80° C., about 25° C. to about 70° C., about 30° C. to about 60° C., about 40° C. to about 60° C., or about 45° C. to about 55° C.

In some embodiments the highly pure hydrocodone product is washed with a solvent, for example water, or an organic solvent (e.g. acetone, methanol, ethanol, propanol, isopropanol, butanol). In some embodiments the highly pure hydrocodone product is washed with a solvent after filtration from the supernatant and before being dried in an oven.

The highly pure hydrocodone product is substantially free from impurities, including solvents, reagents, and byproducts. In some embodiments the highly pure hydrocodone base has a purity of about 95% or greater, 96% or greater, 97% or greater, 98% or greater, 99% or greater, 99.5% or greater, 99.6% or greater, 99.7% or greater, 99.8% or greater, or 99.9% or greater area as measured by high performance liquid chromatography. In some embodiments the highly pure hydrocodone base has a purity of about 95 wt % or greater, 96 wt % or greater, 97 wt % or greater, 98 wt % or greater, 99 wt % or greater, 99.5 wt % or greater, 99.6 wt % or greater, 99.7 wt % or greater, 99.8 wt % or greater, or 99.9 wt % or greater.

In some embodiments the highly pure hydrocodone product comprises about 0.2 wt %, or less, about 0.15 wt % or less, about 0.10 wt % or less, about 0.09 wt % or less, about 0.08 wt % or less, about 0.07 wt % or less, about 0.06 wt % or less, about 0.05 wt % or less, about 0.04 wt % or less, about 0.03 wt % or less, about 0.02 wt % or less, about 0.01 wt % or less, or non-detectable levels of 6α-tetrahydrothebaine (6α-THT). In some embodiments the highly pure hydrocodone product comprises less than about 0.2 wt %, or less, about 0.15 wt % or less, about 0.10 wt % or less, about 0.09 wt % or less, about 0.08 wt % or less, about 0.07 wt % or less, about 0.06 wt % or less, about 0.05 wt % or less, about 0.04 wt % or less, about 0.03 wt % or less, about 0.02 wt % or less, about 0.01 wt % or less, or non-detectable levels of 6,7-dihydrothebaine (6,7-DHT). In some embodiments the highly pure hydrocodone product comprises less than about 0.2 wt %, or less, about 0.15 wt % or less, about 0.10 wt % or less, about 0.09 wt % or less, about 0.08 wt % or less, about 0.07 wt % or less, about 0.06 wt % or less, about 0.05 wt % or less, about 0.04 wt % or less, about 0.03 wt % or less, about 0.02 wt % or less, about 0.01 wt % or less, or non-detectable levels of 6β-tetrahydrothebaine base (6β-THT). In some embodiments, the highly pure hydrocodone product comprises about 0.2 wt %, or less, about 0.15 wt % or less, about 0.10 wt % or less, about 0.09 wt % or less, about 0.08 wt % or less, about 0.07 wt % or less, about 0.06 wt % or less, about 0.05 wt % or less, about 0.04 wt % or less, about 0.03 wt % or less, about 0.02 wt % or less, about 0.01 wt % or less, or non-detectable levels of p-toluene sulfonylhydrazone of hydrocodone (pTSHH). In some embodiments, the highly pure hydrocodone product comprises about 0.2 wt %, or less, about 0.15 wt % or less, about 0.10 wt % or less, about 0.09 wt % or less, about 0.08 wt % or less, about 0.07 wt % or less, about 0.06 wt % or less, about 0.05 wt % or less, about 0.04 wt % or less, about 0.03 wt % or less, about 0.02 wt % or less, about 0.01 wt % or less, or non-detectable levels of total impurities. In some embodiments the highly pure hydrocodone product includes about 0.05 wt % or less, about 0.02 wt % or less, about 0.01 wt % or less, about 0.009 wt % or less, about 0.008 wt % or less, about 0.007 wt % or less, about 0.006 wt % or less, about 0.005 wt % or less, about 0.004 wt % or less, about 0.003 wt % or less, about 0.0025 wt %, about 0.002 wt % or less, about 0.0015 wt % or less, about 0.001 wt % or less, or undetectable levels of codeinone (CDN).

In some embodiments, an optional additional filtering step may be undertaken, for example to attain compliance with good manufacturing practices. In some embodiments the additional filtering step may be performed after the addition of the weak acid and before the addition of the strong base. In some embodiments, the pH of the solution may be adjusted before the additional filtering of the solution. For example, a base (e.g. a strong base) may be added to the solution to attain a pH of, for example, about 3 to about 6, about 4 to about 6, about 4.5 to about 5.5, about 4, about 4.5, about 5, about 5.5, or about 6. The additional filtering step may be performed after addition of an adsorptive medium, such as activated carbon or an ion-exchange resin.

In some embodiments, a highly pure hydrocodone base is prepared as described herein. Highly pure hydrocodone base as described herein may be incorporated into a further composition, e.g., a pharmaceutical formulation. For example, in some embodiments a further composition includes a highly pure hydrocodone base, wherein highly pure hydrocodone base has a purity of about 99.9% area or greater. In some embodiments the highly pure hydrocodone base includes about 0.05 wt % or less, about 0.02 wt % or less, about 0.01 wt % or less, about 0.009 wt % or less, about 0.008 wt % or less, about 0.007 wt % or less, about 0.006 wt % or less, about 0.005 wt % or less, about 0.004 wt % or less, about 0.003 wt % or less, about 0.0025 wt %, about 0.002 wt % or less, about 0.0015 wt %, about 0.001 wt % or less, or undetectable levels of codeinone. In some embodiments a further composition comprises or consists essentially of a pharmaceutical formulation suitable for administration to a patient (e.g. a mammal). A pharmaceutical formulation may comprise highly pure hydrocodone base and one or more excipients. Suitable excipients would be known to a person of ordinary skill in the art and include fillers, glidants, lubricants, and disintegrants.

EXAMPLES

The following examples further describe and demonstrate illustrative embodiments within the scope of the present invention. The examples are given solely for illustration and are not to be construed as limitations of this invention as many variations are possible without departing from the spirit and scope thereof.

Example 1: Experiments Varying Acid and Co-Solvent to Reduce Impurities in Hydrocodone Base These experiments started with a less pure hydrocodone base to evaluate impurity reduction.

General Procedure: Hydrocodone base (15 g), water (75 mL), and acid (1.1 eq.) were charged to a jacketed reactor. The reaction was agitated and heated to ~45-50° C. Sodium hydroxide (18%) was added to pH 4-6. Activated carbon (0.76 g) was added and agitated for ~30 minutes. The reaction was filtered and the carbon cake washed with water (15 mL). The reaction was heated to ~45-50° C. and if necessary, co-solvent was charged (5 mL ethanol or 5 mL butanol). Sodium hydroxide (18%) was added to pH 9.3-9.7 over ~30 minutes. The reaction was cooled to 35-40° C. and agitated for a minimum of 30 minutes. The product was filtered, washed with water (25 mL), and dried overnight at ~50° C. with a slow air sweep.

Hydrocodone Base Initial Route Screening

| | Impurities Present | | | |
|---|---|---|---|---|
| Description | pTSHH/6α-THT RT 13.99 (area %) | 6,7-DHT RT 14.41 (area %) | 6β-THT RT 15.25 (area %) | Yield % |
| Hydrocodone base input | 0.28 | 0.18 | 0.29 | NA |
| Hydrocodone base output (Tartaric Acid weak acid, no co-solvent) | 0.04 | 0.04 | 0.13 | 79 |
| Hydrocodone base output (Tartaric Acid weak acid, Butanol co-solvent) | 0.07 | 0.04 | 0.07 | 73 |
| Hydrocodone base output (Tartaric Acid weak acid, Ethanol co-solvent) | 0.02 | 0.03 | 0.09 | 78 |
| Hydrocodone base output (Acetic Acid weak acid, no co-solvent) | 0.03 | 0.04 | 0.10 | 75 |
| Hydrocodone base output (Acetic Acid weak acid, Butanol co-solvent) | 0.04 | 0.03 | 0.08 | 66 |
| Hydrocodone base output (Acetic Acid weak acid, Ethanol co-solvent) | 0.03 | 0.02 | 0.08 | 72 |

The addition of ethanol or butanol improved the reduction of impurities regardless of acid type.

Example 2: Various Acids with Ethanol and Additional Testing Using Purified Hydrocodone Base These experiments started with purer input and were tested for additional quality attributes.

General Procedure: Hydrocodone base (20 g), water (100 mL), and acid (1.1 eq.) were charged to a jacketed reactor. The reaction was heated to ~45-50° C. and agitated for ~30 minutes. Water (20 mL) was charged to mimic the filter wash. Ethanol (20 mL) was charged. Sodium hydroxide (18%) was added to pH 9.3-9.7 over ~30 minutes. The reaction was cooled to 35-40° C. and agitated for a minimum of 30 minutes. The product was filtered, washed with water (RT, 40 mL), and dried overnight at ~50° C. with a slow air sweep.

Hydrocodone Base Acid Screening

| Description | Yield % | pTSHH/6α-THT RT 13.99 (wt %) | 6,7-DHT RT 14.41 (wt %) | 6β-THT RT 15.25 (wt %) | CDN ppm | ROI % |
|---|---|---|---|---|---|---|
| nPHB Input | — | <0.05 | 0.05 | 0.08 | 14 | — |
| Tartaric Acid | 94 | ND | ND | 0.02 | 10 | 0.70 |
| Acetic Acid | 95 | ND | ND | 0.02 | 10 | 0.14 |
| Sulfuric Acid | 94 | ND | ND | ND | 14 | 0.57 |

ND = Non Detected
ROI = Reduction of impurity

Sulfuric acid did not reduce the codeinone level where the tartaric and acetic acid experiments did (~30% reduction). Acetic acid also had improved ROI results.

Scale-Up/Confirmation Runs

General Procedure: Hydrocodone base (700 g), water (3500 mL), and glacial acetic acid (154 g) were charged to a jacketed reactor. The reaction was heated to ~45-50° C. and agitated until dissolved. The reaction solution was filtered through a polishing filter into a second jacketed reactor. The filter was washed with water (700 mL). Ethanol (700 mL) was charged to the reactor. Sodium hydroxide (18%, ~450 mL) was dosed to pH 9.3-9.7 over ~60 minutes. The reaction was cooled to 35-40° C. and agitated for a minimum of 30 minutes. The product was centrifuged and washed with warm water (35-40° C., 2800 mL). The wet-cake was dried in a vacuum oven overnight at ~50° C. with a slow air sweep and milled in the L1A FitzMill.

Confirmation Runs

| Batch | Assay (odb) % | Yield % | DHT % | pTSHH/6α-THT % | 6,7-DHT % | 6β-THT % | ATA % | CDN ppm | ROI % |
|---|---|---|---|---|---|---|---|---|---|
| Input Hydrocodone Base Material A | 99.2 | | ND | 0.05 | <0.05 | 0.07 | ND | NT | |
| Purified Hydrocodone Base Material A | 100.6 | 85 | ND | ND | ND | ND | ND | 8 | 0.02 |
| Input Hydrocodone Base Material B | 101.8 | | ND | 0.05 | <0.05 | 0.09 | ND | NT | |
| Purified Hydrocodone Base Material B | 100.5 | 88 | ND | ND | ND | ND | ND | 12 | 0.03 |

-continued

| Batch | Assay (odb) % | Yield % | DHT % | pTSHH/ 6α-THT % | 6,7-DHT % | 6β-THT % | ATA % | CDN ppm | ROI % |
|---|---|---|---|---|---|---|---|---|---|
| Input Hydrocodone Base Material C | 99.0 |  | ND | <0.05 | <0.05 | 0.08 | ND | NT |  |
| Purified Hydrocodone Base Material C | 100.6 | 87 | ND | ND | ND | ND | ND | 9 | 0.02 |

ND = Non Detected
NT = Not Tested (Input hydrocodone base typically has ~20 ppm of codeinone)
ATA = thebaine
CDN = codeinone
DHT = dihydrothebainone It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method of recovering a highly pure hydrocodone base from an impure hydrocodone preparation, the method comprising:
   contacting the impure hydrocodone preparation with a weak acid in water to form a solution;
   charging the solution with an organic solvent before the addition of the strong base;
   adding a strong base to the solution in an amount sufficient to precipitate the highly pure hydrocodone base.

2. The method of claim 1, wherein the organic solvent is an alcohol.

3. The method of claim 2, wherein the alcohol is selected from the group consisting of: methanol, ethanol, propanol, isopropanol, butanol, tert-butyl alcohol, or a mixture of any of the foregoing.

4. The method of claim 2, wherein the alcohol is ethanol or butanol.

5. The method of claim 1, where the highly pure hydrocodone base comprises less than 0.05 wt % 6α-tetrahydrothebaine (6a-THT).

6. The method of claim 1, where the highly pure hydrocodone base comprises less than 0.05 wt % 6,7-dihydrothebaine.

7. The method of claim 1, where the highly pure hydrocodone base comprises less than 0.05 wt % 6β-tetrahydrothebaine base.

8. The method of claim 1, where the highly pure hydrocodone base comprises less than 0.0025 wt % codeinone.

9. The method of claim 1, wherein the highly pure hydrocodone base has a purity of about 99.9% area as measured by high performance liquid chromatography.

* * * * *